United States Patent [19]

Gatten et al.

[11] Patent Number: 5,183,486
[45] Date of Patent: Feb. 2, 1993

[54] APPARATUS FOR DEGASSING A LIQUID

[75] Inventors: Ronald A. Gatten, Pleasanton; Leslie A. Miller, San Jose; Thomas J. McCall, Jr., Fremont; Vance J. Nau, Cupertino, all of Calif.

[73] Assignee: Spectra-Physics, Inc., San Jose, Calif.

[21] Appl. No.: 622,999

[22] Filed: Dec. 4, 1990

[51] Int. Cl.⁵ ............................................. B01D 19/00
[52] U.S. Cl. ..................................... 55/159; 55/386; 55/197; 55/158; 210/198.2; 210/635
[58] Field of Search ................. 55/16, 55, 67, 386, 55/159, 158, 208, 197; 210/635, 198.2; 73/61.1 C, 864.81

[56] References Cited

U.S. PATENT DOCUMENTS

| | | | |
|---|---|---|---|
| 3,377,778 | 4/1968 | Gaertner | 55/55 |
| 4,079,009 | 3/1978 | Seiler et al. | 210/198.2 |
| 4,271,697 | 6/1981 | Mowery | 210/198.2 |
| 4,293,418 | 10/1981 | Fujii et al. | 55/158 |
| 4,374,656 | 2/1983 | Schrenker et al. | 55/170 |
| 4,469,495 | 9/1984 | Hiraizumi et al. | 55/189 |
| 4,505,149 | 3/1985 | Trumbore | 73/61.1 C |
| 4,629,561 | 12/1986 | Shirato et al. | 210/198.2 |
| 4,651,087 | 3/1987 | Shirato et al. | 324/71.4 |
| 4,652,364 | 3/1987 | Shirato et al. | 210/87 |
| 4,728,344 | 3/1988 | Stacy | 55/67 |
| 4,729,773 | 3/1988 | Shirato et al. | 55/158 |
| 4,794,954 | 1/1989 | Tokuda et al. | 138/30 |
| 4,819,478 | 4/1989 | Melcher | 210/635 |
| 4,986,837 | 1/1991 | Shibata | 55/159 |
| 4,988,447 | 1/1991 | Hellinger | 210/198.2 |
| 5,053,060 | 10/1991 | Kopfsill | 55/208 |

FOREIGN PATENT DOCUMENTS

| | | | |
|---|---|---|---|
| 0360604 | 3/1990 | European Pat. Off. | 73/61.1 C |
| 257810 | 12/1985 | Japan | 55/55 |
| 122260 | 5/1990 | Japan . | |
| 2097281 | 11/1982 | United Kingdom | 55/55 |

OTHER PUBLICATIONS

Bakalyar et al, *The Role of Dissolved Gases in High-Performance Liquid Chromatography*, J. Chromatog. vol. 158, pp. 277-293 (1978).
*Shodex Operation Manual No. 781 for Shodex DEGAS KT-Series Degassing Device*, available from Showa Denko K.K., Speciality Chemicals Division, Shodex Separation & HPLC Group, 13-9, Shiba Daimon 1--Chome, Minato-Ku, Tokyo 105, Japan 1110.

*Primary Examiner*—Bernard Nozick
*Attorney, Agent, or Firm*—Killworth, Gottman, Hagan & Schaeff

[57] ABSTRACT

Methods and apparatus for effective vacuum degassing of a liquid are provided for liquid chromatography. The bottles with the liquid are mounted above the vacuum degassing unit to provide a head pressure to the LC pump and physical stability to the bottles. The liquid is heated in the vacuum chamber by a radiator of electromagnetic energy (in one embodiment, infra-red light). Alternatively the liquid is heated before it enters the vacuum chamber. The liquid is in an agitated state in the vacuum chamber. In one variation, the liquid is conducted through the vacuum chamber through tubes wound around bobbins so as to expose a greater portion of the surface area of the tubes to vacuum. Circuitry stops the vacuum pump for a duration of a chromatographic run. The circuitry controls the LC pump and the vacuum pump so as to optimize the chromatographic conditions in the liquid chromatography analytical system. The autosampler of the analytical system includes a vacuum degasser for degassing the resident solvents of the autosampler. Alternatively, the vacuum degassing unit for degassing the mobile phase is used to degas the resident solvents. The analytical system has its own vacuum chamber for extracting a gas from the sample to be analyzed. The extracted gas is used to produce chromatographic information. Components of a mixed solvent are mixed before the solvent is degassed. The vacuum chamber of the degassing unit is used in one variation to dissolve a selected gas in a mobile phase for use in chromatographic analysis. A method is provided for testing a conduit for conducting a liquid through the vacuum chamber. A selected gas is put in the conduit instead of the solvent, a vacuum level is created, and the time of decay of the vacuum level is measured to determine the contamination of the walls of the conduit.

4 Claims, 8 Drawing Sheets

FIG-1

PRIOR ART

FIG-2

PRIOR ART

FIG-3

PRIOR ART

APPARATUS FOR DEGASSING A LIQUID

BACKGROUND OF THE INVENTION

The present invention relates to degassing a liquid, and more particularly to vacuum degassing of a liquid.

Figure 1:
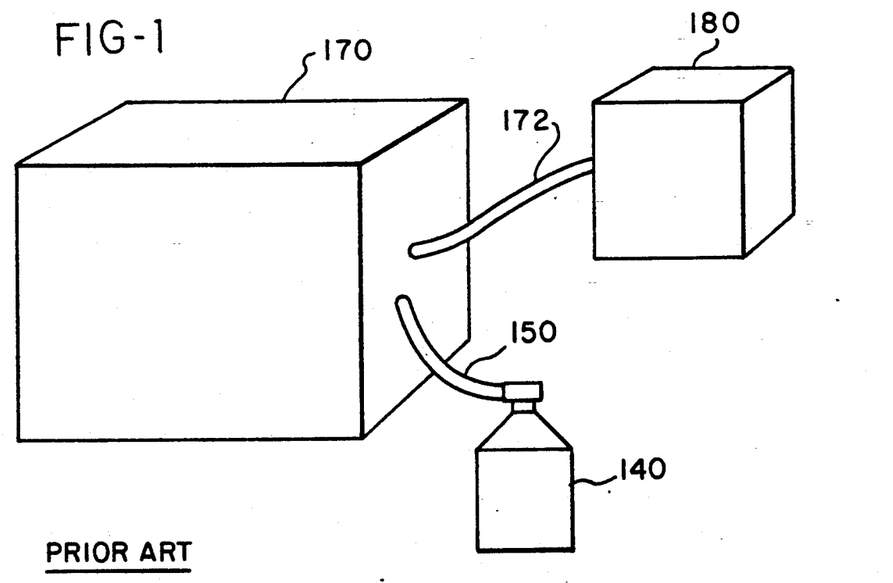
FIG. 1 shows a block diagram of a prior art system including a degasser and a liquid chromatography analytical system.

Degassing is practiced in liquid chromatography to extract air from mobile phase solvents since the presence of air (particularly oxygen) interferes with chromatographic analysis. See Bakalyar, Bradley and Honganen, *The Role of Dissolved Gases in High-Performance Liquid Chromatography*, Journal of Chromatography, 158 (1978) 277–293. As is shown in FIG. 1, the solvent is conducted from bottle 140 via tubing 150 to a degasser 170 where the solvent is degassed. The degassed solvent is conducted via tubing 172 to a liquid chromatography analytical system (LC analytical system) 180 for use as a mobile phase.

Figure 2:
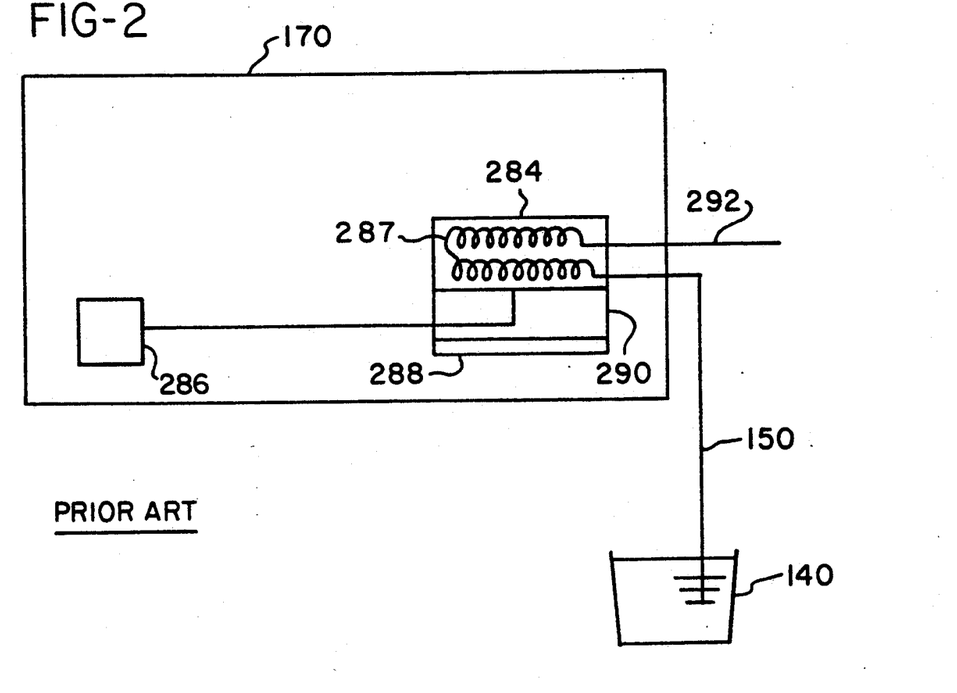
FIG. 2 shows a schematic diagram of a prior art degasser.

FIG. 2 shows a schematic diagram of a Shodex DEGAS KT-Series Degasser 170 available from Shodex Group of Tokyo, Japan. The solvent is pumped by a liquid chromatography pump (LC pump, not shown in FIG. 2) from bottle 140 via tubing 150 to a vacuum chamber 284. A vacuum pump 286 creates vacuum in vacuum chamber 284. As the solvent flows through tubing 287, gas dissolved in the solvent goes out through the wall of tubing 287 made of a special macromolecular film, and the solvent is thus degassed. A heater 288 under a vacuum chamber base 290 can be used to heat the solvent in vacuum chamber 284 to increase the effectiveness of degassing. The degassed solvent is pumped to a LC analytical system (not shown in FIG. 2) via tubing 292. See *Shodex Operation Manual No. 781 for Shodex DEGAS KT-Series Degassing Device* available from SHOWA DENKO K.K., Specialty Chemicals Division, Shodex (Separation & HPLC) Group, 13-9, Shiba Daimon 1-Chome, Minato-ku, Tokyo 105, Japan.1110

Figure 3:
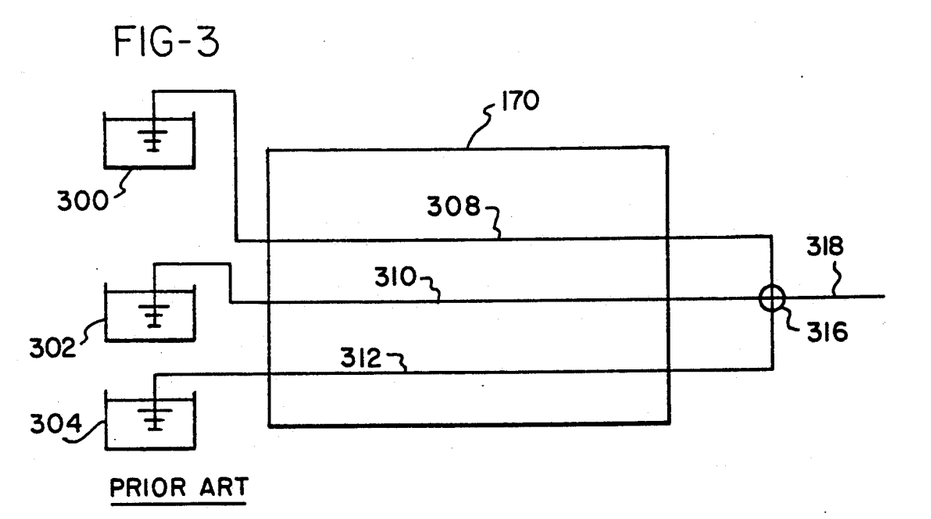
FIG. 3 shows a schematic diagram of a prior art degasser used to degas components of a mixed solvent.

Shodex degasser 170 of FIG. 2 can be used to degas components of a mixed solvent as is schematically shown in FIG. 3. Each of bottles 300, 302 and 304 contains a component of the solvent. The components are conducted via respective tubings 308, 310 and 312 through degasser 170 in which each component is degassed. The degassed components are mixed, in a portion 316 of the tubing, into a solvent which is conducted to a liquid chromatography analytical system (not shown in FIG. 3) via tubing 318.

It is desirable to provide effective methods and apparatus for degassing of a liquid.

SUMMARY OF THE INVENTION

The present invention provides methods and apparatus for effective degassing of a liquid. The invention also provides temperature control of the liquid and effective arrangement of containers with the liquid. The invention can be used for preparing a mobile phase for liquid chromatography and for preparing a sample for analysis by liquid chromatography or by other methods. Methods for testing apparatus of the invention are also provided.

A module for conditioning a liquid is provided comprising means for degassing the liquid and a holder for holding a container with the liquid. The holder is mounted on top of the degassing means. Such an arrangement, when used to degas a mobile phase, increases the physical stability of the container.

A pump is provided for pumping a liquid from a container. The pump calculates the amount of liquid pumped and the amount of liquid remaining in the container. The amount of remaining liquid is displayed.

A vacuum degassing unit for degassing a liquid is provided comprising means for conducting the liquid through a vacuum chamber and a radiator for radiating electromagnetic energy to be transmitted to the conducting means. In some embodiments, the radiator is adapted to heat the liquid or the conducting means by the electromagnetic energy. Such a radiator is more efficient for heating than the conventional heat-radiating heater because vacuum in the vacuum chamber is not a good conductor of heat but is a good conductor of electromagnetic energy.

A vacuum degassing unit for degassing a liquid is provided in which a heater heats the liquid before the liquid enters a vacuum chamber.

A vacuum degassing unit for degassing a liquid is provided in which the liquid is in a state of agitation in a vacuum chamber. In some embodiments, when the vacuum chamber is at vacuum, gas is extracted from the portions of the liquid adjacent to the walls of the tubing for conducting the liquid. The liquid is agitated so as to bring other portions of the liquid close to the walls of the tubing. Effectiveness of degassing is increased thereby.

A vacuum degassing unit for degassing a liquid is provided in which the liquid is conducted through a vacuum chamber via a tube. The tube is wound in coils around a bobbin. The adjacent coils of the tube are spaced from each other. In some embodiments, such a construction increases the tubing surface area exposed to vacuum in the vacuum chamber and thus makes degassing more efficient.

A vacuum degassing unit for degassing a solvent for use in a liquid chromatography analytical system is provided comprising a vacuum chamber and a pump for creating a vacuum in the chamber. A means is provided for stopping the pump or for restricting the pump operation for a duration of a chromatographic run. It is desirable in some applications to stop the vacuum pump for a duration of the run so as not to change the oxygen level in the solvent during the run.

An apparatus for degassing a solvent is provided comprising a vacuum chamber, a first pump for creating a vacuum in the chamber, and a second pump for pumping the solvent through the chamber. The first and the second pumps are controlled in response to chromatographic conditions in the LC analytical system so as to optimize the conditions. In one embodiment, the second pump is controlled so as to adjust the flow rate of the solvent through the vacuum chamber so as to optimize the chromatographic conditions.

An autosampler is provided comprising means for injecting a sample into a mobile phase, a vacuum degassing unit for degassing a solvent, and means for conducting the degassed solvent through the injecting means. In one embodiment, the solvent is a flush solvent used to flush the injecting means. In another embodiment, the solvent is a diluent or a reagent used for sample dilution or chemical transformation.

An autosampler is provided comprising means for connecting a sample container to a vacuum degassing unit and means for connecting the vacuum degassing unit to an injector valve. In one embodiment, the autosampler is used to degas a sample to be analyzed by liquid chromatography.

A liquid chromatography analytical system for analyzing a sample is provided comprising a vacuum chamber for extracting a gas from the sample. The extracted gas is used for producing chromatographic information.

A method is provided for providing a mixed mobile phase. The components of the mobile phase are mixed, the mixed mobile phase is placed into a vacuum chamber, degassed, and conducted to an LC analytical system. Mixing the components of the mobile phase before degassing the mobile phase is advantageous when the solubility of gases in the mixed mobile phase is lower than the solubility of the gases in the components.

A method is provided for testing the conduit (such as tubing or a membrane) for conducting a liquid to be degassed through the vacuum chamber. Namely, a selected gas is introduced into the conduit. A predetermined level of vacuum is reached in the chamber. As the vacuum level decays, the time of decay is measured. The condition of the conduit is determined from the time of decay. For example, when the walls of the tubing become contaminated by particles suspended in the liquid, the time of decay is longer. The contaminated condition of the tubing walls is determined from the increased time of decay.

A method is provided for using a vacuum chamber for the "reverse" purpose of dissolving a gas in the mobile phase. It is sometimes advantageous to dissolve some gas in the mobile phase. The gas is put into the vacuum chamber under pressure so as to dissolve at least a portion of the gas in the mobile phase. The mobile phase is conducted to the analytical system.

Other aspects and objects of the invention will become apparent from the following description, the drawings, and the appended claims.

DESCRIPTION OF THE PREFERRED EMBODIMENTS

Figure 4:
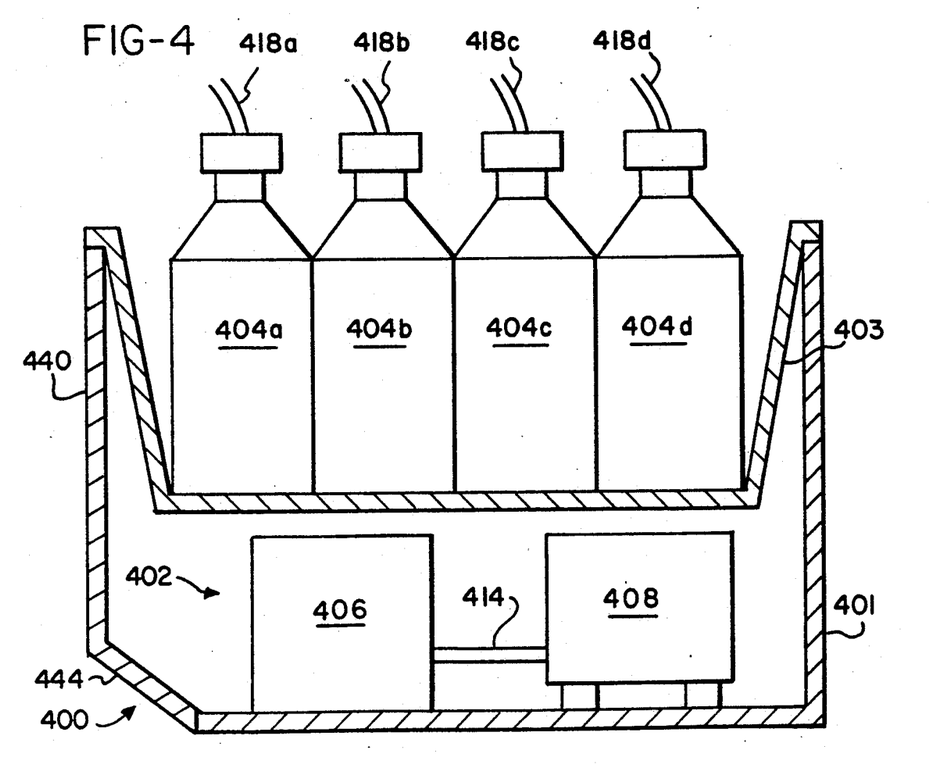
FIG. 4 shows a cross-section of a solvent conditioning module according to this invention.

FIG. 4 shows a cross-section of "Pumpmate TM" (trade-mark of Spectra-Physics, Inc., of San Jose, Calif.), a solvent conditioning module for degassing a mobile phase solvent and for controlling the temperature of the solvent. Solvent conditioning module 400 comprises a housing 401, a vacuum degassing unit 402 and a holder 403 on top of vacuum degassing unit 402. Holder 403 holds bottles 404 containing components of the solvent. (Bottles 404 are not part of solvent conditioning module 400.) Holder 403 is large enough to contain, in addition to bottles 404, a spill whose volume is at least 1.1 times the volume of the contents of any one of bottles 404. In one variation, each bottle 404 is a 1-liter bottle, and holder 403 is large enough to contain a 1.1-liter spill in addition to bottles 404. Holder 403 can be lifted and removed for easy cleaning.

Vacuum degassing unit 402 comprises a vacuum chamber 406 and a vacuum pump 408 which creates a vacuum in vacuum chamber 406 by pumping air out via a path 414. The solvent components are conducted from the respective bottles 404 via the respective tubing 418 to vacuum chamber 406.

A door 440 of housing 401 is hinged on top by hinges (not shown). Door 440 can be opened by applying upward pressure to a slanted door portion 444.

Figure 5:
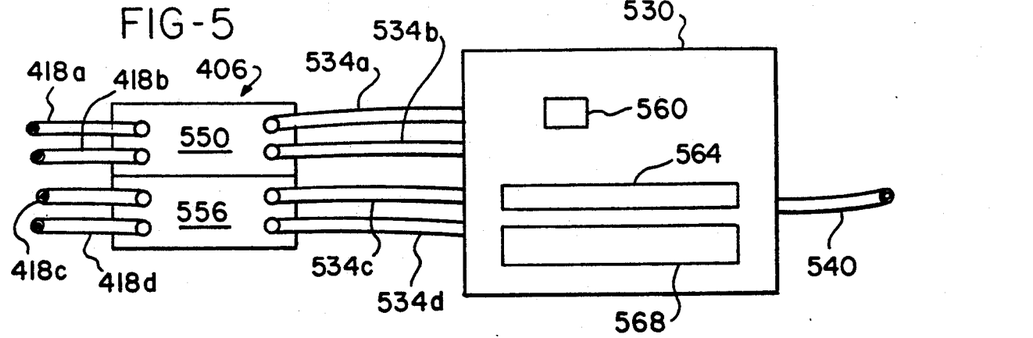
FIG. 5 shows schematically a side view of a vacuum chamber and a liquid chromatography pump according to this invention.

FIG. 5 shows a side view of vacuum chamber 406 and of a liquid chromatography pump (LC pump) 530. LC pump 530 outside solvent conditioning module 400 pumps the solvent component from bottle 404a through tubing 418a to vacuum chamber 406 where the solvent component is degassed, and then through tubing 534a into LC pump 530 itself. Likewise, LC pump 530 pumps solvent components from each bottle 404b, 404c, 404d through respective tubing 418b, 418c, 418d to vacuum chamber 406, and then through respective tubing 534b, 534c, 534d into LC pump 530 itself. Tubing 418 is laced to a wall of housing 401 so that tubing 418 cannot be easily snagged. Tubing 534 passes through an opening (not shown) between door 440 and a wall of housing 401. The solvent components from different bottles 404 are mixed inside pump 530 in precise proportions by means of standard solvent proportioning techniques such as described in *SP*8800/8810 *LC Pump Operators Manual* (Spectra-Physics, 1987, Part Number A0099-235 9/88 D) available from Spectra-Physics of San Jose, Calif. and hereby incorporated by reference herein. LC pump 530 then pumps the mixed solvent through tubing 540 to an LC analytical system (not shown in FIGS. 4 and 5).

Vacuum chamber 406 is constructed in one embodiment of two cartridges: top cartridge 550 for degassing the solvent components from bottles 404a and 404b, and bottom cartridge 556 for degassing the solvent components from bottles 404c and 404d. The interiors of cartridges 550 and 556 communicate so that both cartridges 550 and 556 are at vacuum at the same time.

LC pump 530 includes for control purposes a software-programmed microprocessor 560, a keyboard 564 and a display 568 to allow the user to monitor the level of the solvent components in bottles 404. When the solvent components are placed in respective bottles 404, the user enters the initial level of each solvent component on keyboard 564. As LC pump 530 pumps the solvent, microprocessor 560 calculates the amount of each solvent component pumped out from bottles 404. The levels of the solvent components remaining in bottles 404 are displayed on display 568 and are continuously updated. When solvent conditioning module 400 is about to run out of at least one solvent component, LC pump 530 generates a signal to alarm the human operator.

In one embodiment, a weight sensor sensing the weight of bottles 404 is used to determine the initial level of each solvent component in each bottle 404. In one embodiment, a separate weight sensor is used for each bottle 404. The weight from each sensor is entered into LC pump 530 automatically.

Solvent conditioning module 400 is used to condition solvents having less than four components (including solvents having only one component). Correspondingly, less than four bottles 404 are used, or different bottles 404 are filled by the same component. Other variations of solvent conditioning module 400 can accommodate more than four bottles 404. Still other variations can accommodate only one, two or three bottles 404.

In some variations, the solvent component from each bottle 404 is pumped through vacuum chamber 406 by a separate LC pump, and the solvent components are mixed at the outputs of the respective LC pumps.

In some variations, the LC pump (or pumps) 530 is connected to tubing 418 upstream of vacuum chamber 406 in the flow path of the solvent. The solvent (or solvent components) in LC pump 530 is in an undegassed state. Gas bubbles in the solvent get hung up in check valves and pistons of LC pump 530 and disrupt the flow rate of LC pump 530. Thus placing LC pump 530 downstream of vacuum chamber 406 is advantageous.

Figure 6:
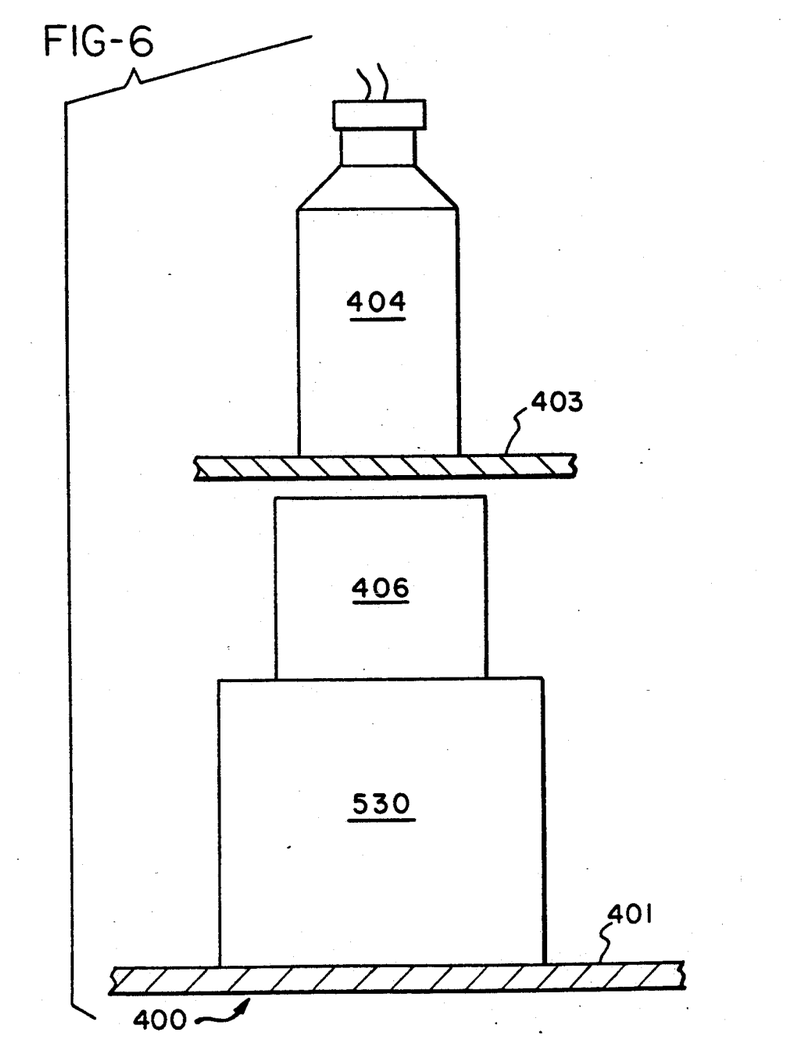
FIG. 6 shows a cross-section of another solvent conditioning module according to this invention.

FIG. 6 shows a portion of a cross-section of a variation of solvent conditioning module 400 in which LC pump 530 is placed under vacuum chamber 406. Such a construction allows closer coupled tubing between vacuum chamber 406 and LC pump 530.

Mounting the holder 403 with bottles 404 above vacuum degassing unit 402 provides head pressure into LC pump 530 and thus improves the solvent flow from bottles 404 to the LC analytical system. Holder 403 is removable for cleaning. Tubing 418 cannot be easily snagged. Holder 403 provides physical stability to bottles 404 so that bottles 404 are less likely to slide off or tip over. Holder 403 is made of an essentially inert material. Tubing 418, tubing 534, and tubing 540 are typically made of Teflon (a registered trademark of the DuPont Corporation). Degassing unit 402 is sealed within housing 401 so that a liquid spill from bottles 404 does not enter degassing unit 402 and its circuitry.

Figure 7:
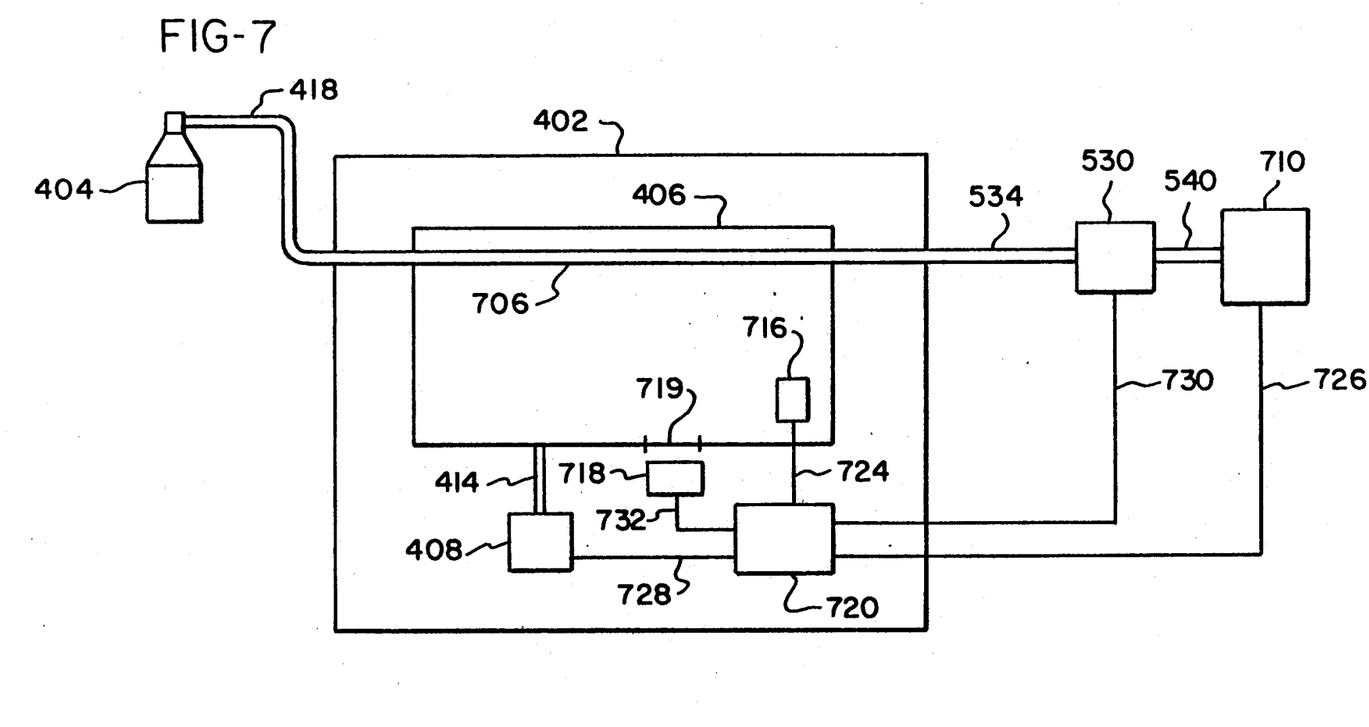
FIG. 7 shows a schematic diagram of a vacuum degassing unit according to this invention.

FIG. 7 shows a schematic diagram of vacuum degassing unit 402. The solvent (or solvent component) is conducted from bottle (or bottles) 404 by tubing 418 to vacuum chamber 406. Only one bottle 404 is shown for simplicity. The solvent is degassed in vacuum chamber 406 while in a solvent conduit 706. Solvent conduit 706 is gas permeable tubing. In an alternative embodiment, when vacuum degassing unit 402 degasses one solvent component, solvent conduit 706 is a membrane; the solvent component flows above the membrane, and a vacuum is created below the membrane. In either case, solvent conduit 706 is made of an essentially inert material permeable to gas, typically of Teflon. The walls of solvent conduit 706 are thinner than the walls of tubing 418. The degassed solvent is conducted by tubing 534 to LC pump 530 and from there by tubing 540 to LC analytical system 710. Vacuum pump 408 creates a vacuum in vacuum chamber 406 by pumping air out via path 414. A vacuum sensor 716 senses the level of vacuum in vacuum chamber 406. A light radiator 718, typically an infra-red light bulb, radiates infra-red light toward solvent conduit 706 when it is desirable to heat the solvent and solvent conduit 706. Heating the solvent is sometimes advantageous in degassing because it may decrease the solubility of gas in the solvent. See Bakalyar, Bradley and Honganen, supra, hereby incorporated by reference herein, at page 280. Heating solvent conduit 706 is desirable because it increases the permeability of the Teflon walls of conduit 706 to gas. The light is transmitted through clear window 719 in the wall of vacuum chamber 406. Light radiator 718 heats in vacuum more efficiently than a conventional heat-radiating heater because vacuum is not a good conductor of heat but is a good conductor of infra-red light.

In some variations, light radiator 718 is placed inside vacuum chamber 406. In some variations, light radiator 718 radiates other types of electromagnetic energy rather than infra-red light.

Circuitry 720 receives signals from vacuum sensor 716 and LC analytical system 710 via respective signal paths 724 and 726 and controls vacuum pump 408, LC pump 530 and light radiator 718 via respective signal paths 728, 730 and 732. In particular, circuitry 720 provides indications to the operator when vacuum sensor 716 senses that a proper level of vacuum has been reached in vacuum chamber 406. Circuitry 720 receives, from LC analytical system 710 via signal path 726, data regarding chromatographic conditions in analytical system 710 and controls vacuum pump 408 and LC pump 530 so as to optimize the chromatographic conditions. For example, if the level of oxygen in the mobile phase solvent in analytical system 710 is too high, circuitry 720 slows down LC pump 530 so as to lower the flow rate of the solvent through vacuum chamber 406 allowing more oxygen to be extracted during degassing. In one variation, circuitry 720 detects an occurrence of a chromatographic run from the signals from LC analytical system 710 via signal path 726, and stops vacuum pump 408 for the duration of the run so as not to change the oxygen level in the solvent during the run. Changes in the oxygen level in the solvent during the run could lead to a baseline drift of a chromatographic detector (not shown). See Bakalyar, Bradley and Honganen, supra.

Figure 8:
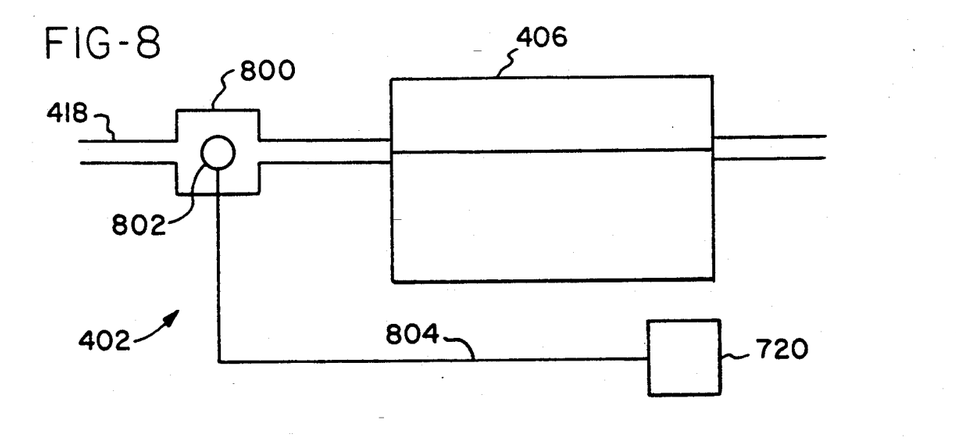
FIG. 8 shows a schematic diagram of a portion of another vacuum degassing unit according to this invention.

FIG. 8 shows a schematic diagram of a portion of a variation of vacuum degassing unit 402. A chamber 800 hooks up to tubing 418 which connects bottles 404 to vacuum chamber 406. Ceramic heating element 802 is positioned in the flow path of the solvent (or solvent component) upstream of vacuum chamber 406. Heating element 802 comes in contact with the solvent and heats the solvent more efficiently than a heat-radiating heater in a vacuum chamber. The temperature level of heater 802 is controlled by circuitry 720 via signal path 804.

Figure 9:
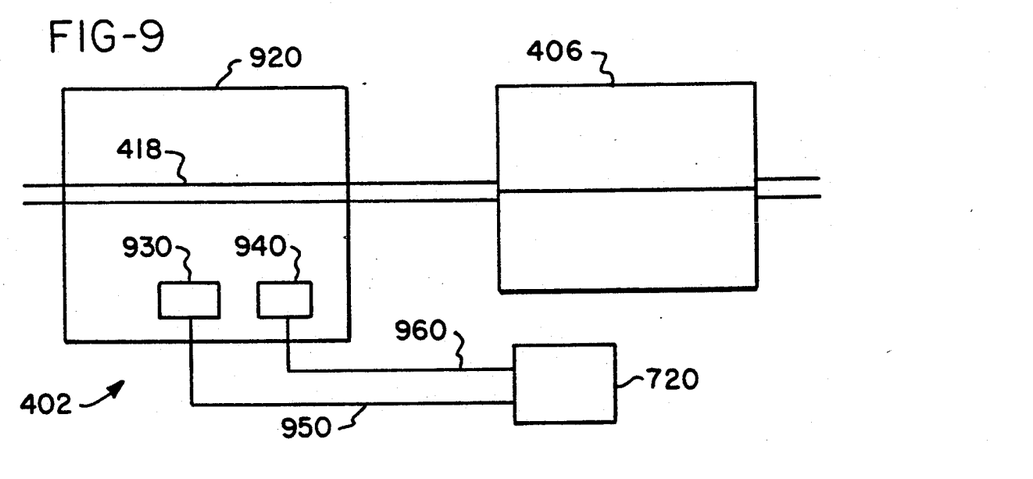
FIG. 9 shows a schematic diagram of a portion of another vacuum degassing unit according to this invention.

In the embodiment of FIG. 9, tubing 418 passes through a thermal chamber 920 maintained at atmospheric pressure. The air in thermal chamber 920 is heated by a heat-radiating heater 930. Tubing 418 transmits the heat to the solvent. A fan 940 circulates the air in thermal chamber 920 to transmit the heat to the solvent more efficiently. Circuitry 720 controls heater 930 and fan 940 via respective signal paths 950 and 960. The air in thermal chamber 920 conducts heat more efficiently than the air at vacuum in vacuum chamber 406. Thus, heating the solvent in thermal chamber 920 by heat-radiating heater 930 is more efficient than heating the solvent in vacuum chamber 406 by such a heater.

Figure 10:
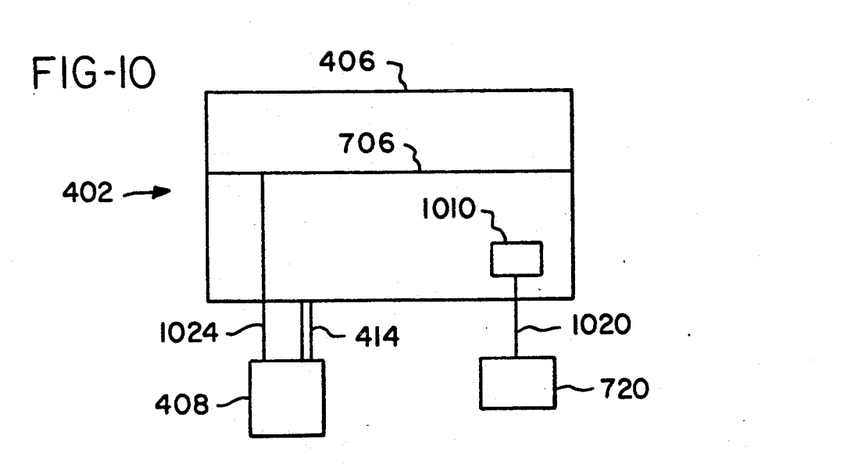
FIG. 10 shows a schematic diagram of another vacuum degassing unit according to this invention.

FIG. 10 shows a schematic diagram of a portion of a variation of degassing unit 402. When vacuum chamber 406 is at vacuum, gas is extracted from the portions of the solvent close to the walls of solvent conduit 706. It may be desirable to agitate the solvent in conduit 706 so as to bring other portions of the solvent closer to the walls of conduit 706. An ultrasonic device 1010 emits ultrasound waves that impact the solvent in conduit 706 and thereby agitate the solvent. The ultrasonic energy of ultrasonic device 1010 is controlled by circuitry 720 via a signal path 1020.

Connector 1024 connecting vacuum pump 408 to conduit 706 provides another means for agitating the solvent. In this variation, vacuum pump 408 vibrates when operated. Connector 1024 transmits the vibrations of vacuum pump 408 to conduit 706. The vibrations agitate the solvent.

Figure 11:
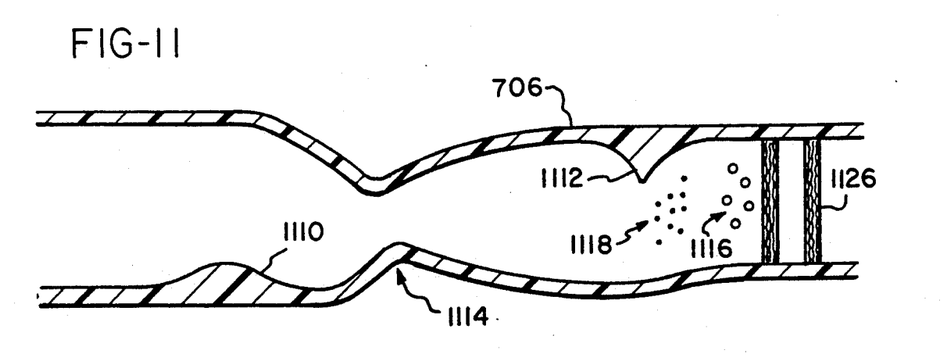
FIG. 11 shows a cross-section of a solvent conduit according to this invention.

FIG. 11 shows, in cross-section, one embodiment of solvent conduit 706. Solvent conduit 706 is Teflon tubing. Its inner surface has an uneven portion so as to agitate the solvent as it flows by. Namely, the inner surface of conduit tubing 706 includes bumps such as bump 1110 and/or ridges such as ridge 1112. Conduit tubing 706 also may comprise a pinched portion 1114 to further agitate the solvent. Glass beads 1116 and magnetic particles 1118 may be provided inside conduit tubing 706 in order to further agitate the solvent. Magnetic particles 1118 are agitated by a conventional magnetic stirrer (not shown) located adjacent tubing 706. A portion of conduit tubing 706 downstream of glass beads 1116 and magnetic particles 1118 is packed by a column packing material 1126, the same material that is used to pack a chromatography column (not shown). In one variation, magnetic particles 1118 are held in place by an external magnetic field.

Figure 12:
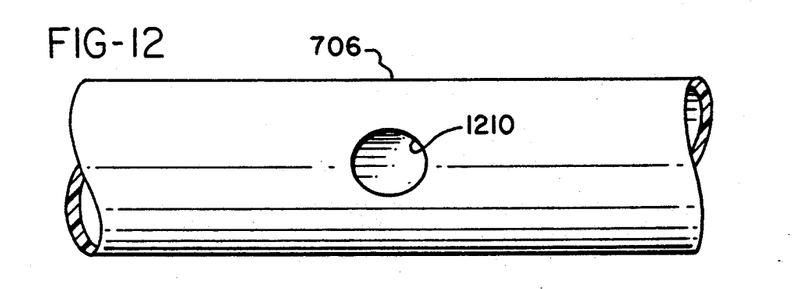
FIG. 12 shows a side view of another solvent conduit according to this invention.

Conduit tubing 706 of FIG. 12 in another embodiment has an internal sealed off section (hole) 1210 to further agitate the solvent as it passes through. In general, conduit tubing 706 can be deformed in many ways to agitate the solvent.

Figure 13:
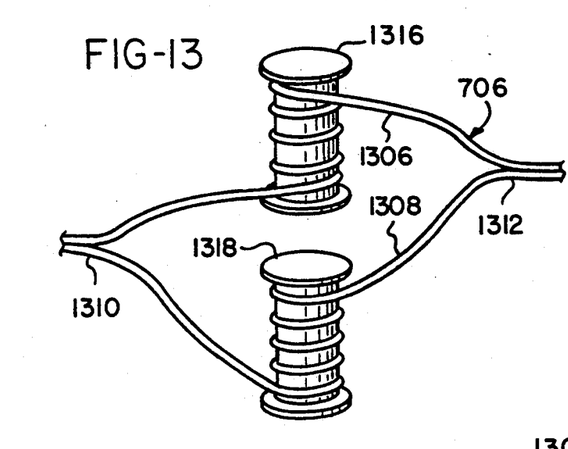
FIG. 13 shows schematically another solvent conduit according to this invention.

To increase the amount of gas extracted from the solvent in a vacuum chamber, it is desirable to maximize the conduit tubing surface area exposed to vacuum. To that end, conduit tubing 706 of FIG. 13 is separated into two tubes 1306 and 1308 which interconnect portions 1310 and 1312 of conduit tubing 706. Tube 1306 is wound in coils around bobbin 1316, and tube 1308 is wound in coils around bobbin 1318. Bobbins 1316 and 1318 serve to separate the coils of tubes 1306 and 1308 so that the surfaces of the coils do not touch but are exposed to the surrounding vacuum. Namely, the adjacent coils of tube 1306 are spaced from each other, and the adjacent coils of tube 1308 are spaced from each other. Further, the coils of tube 1306 are spaced from the coils of tube 1308. In other variations, more than two tubes such as tube 1306 and tube 1308 are used, with each tube wound around its own bobbin.

Figure 14:
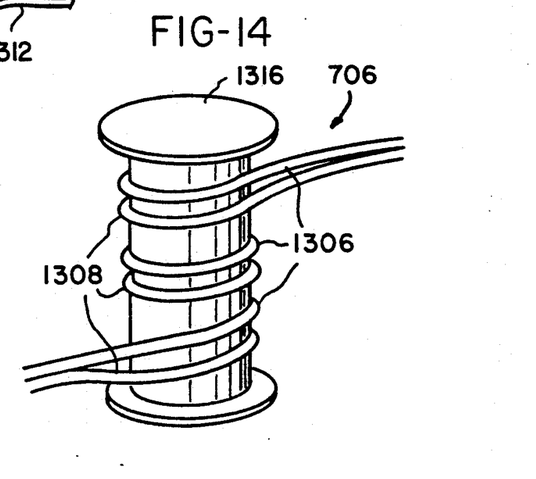
FIG. 14 shows schematically another solvent conduit according to this invention.

In the variation of FIG. 14, both tubes 1306 and 1308 are wound around the same bobbin 1316. The coils of tube 1306 alternate with the coils of tube 1308. In another variation, conduit 706 comprises only one tube wound in coils around a bobbin so that the adjacent coils of the tube are spaced from each other. In other variations, conduit 706 comprises more than two tubes separated into groups of one or more tubes each, the tubes of each group wound around a respective bobbin.

In some variations, conventional wire structures hold the coils of the tubes of conduit tubing 706 so as to separate the coils from each other.

Figure 15:
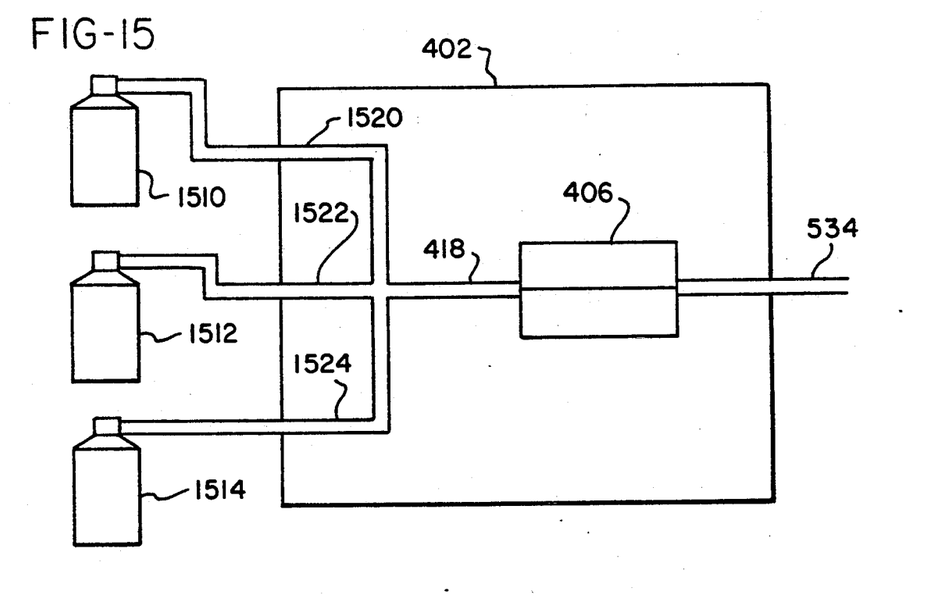
FIG. 15 shows a schematic diagram of a vacuum degassing unit of this invention used to degas a mixed mobile phase.

Mixed mobile phase solvents are often used in liquid chromatography. In some cases, the solubility of certain gases in a mixed solvent is lower than the solubility of the gases in the components forming the solvent. It is then desirable to mix the components before degassing the solvent rather than to degas each component and then mix the degassed components. This degassing method is illustrated schematically in FIG. 15. Bottles 1510, 1512, and 1514 each contain a separate component of a mobile phase solvent. The components flow through respective tubing 1520, 1522, and 1524 and mix in tubing 418 before entering vacuum chamber 406. The mixed solvent is degassed in vacuum chamber 406 and is then conducted to LC analytical system 710 (not shown in FIG. 15).

Figure 16:
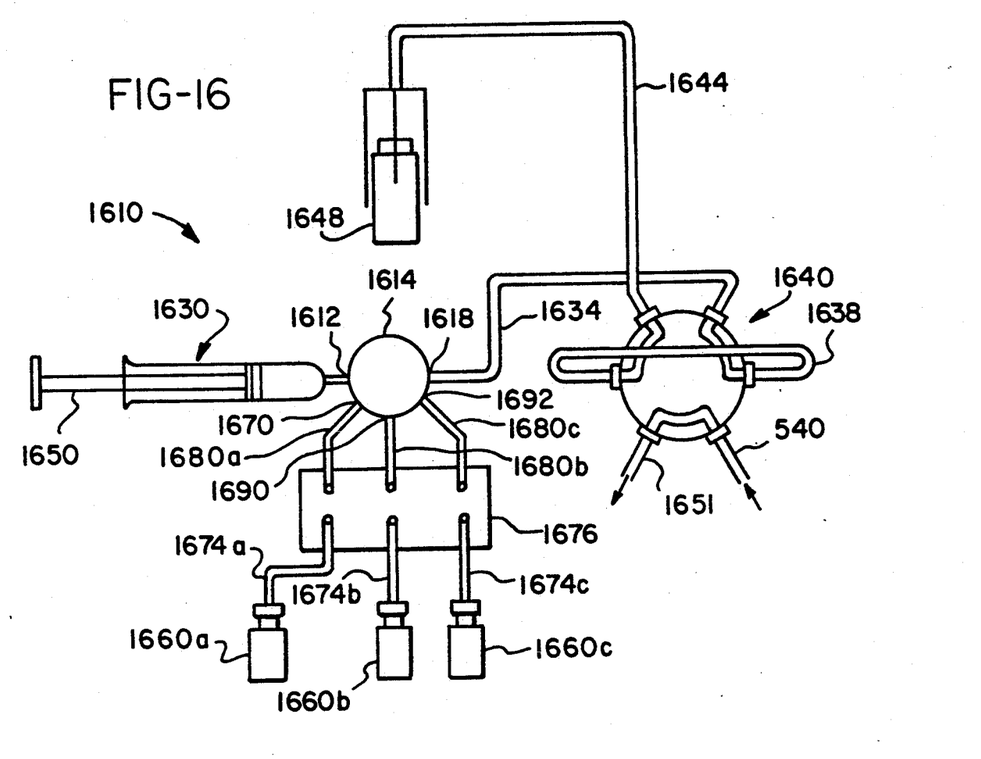
FIG. 16 shows a schematic diagram of an autosampler according to this invention.

FIG. 16 shows schematically an autosampler 1610 that forms part of LC analytical system 710. When a port 1612 of a multiport valve 1614 is connected to a port 1618, a syringe 1630 is connected to a tube 1634 and, through a loop 1638 of an injector valve 1640, to a tube 1644 and a sample container 1648. A syringe barrel 1650 is withdrawn by a predetermined distance so that a precisely metered amount of the sample is drawn from sample container 1648 through tube 1644 into loop 1638. Injector valve 1640 is then rotated to inject the sample in loop 1638 into the mobile phase arriving via tubing 540. See *SP8780/8775 Autosampler Operators manual* (Spectra-Physics, 1987, Part Number A0099-263 8/87 A) available from Spectra-Physics of San Jose, Calif. and hereby incorporated by reference herein. The mobile phase carries the sample via tubing 1651 to a chromatography column (not shown) for separation and analysis.

Sample container 1648 is then removed and replaced by a waste container (not shown). Syringe barrel 1650 is pushed in to expel the remaining syringe contents through tube 1634 and tube 1644 into the waste container. Autosampler 1610 is then flushed using the flush solvent in bottle 1660a. Namely, multiport valve 1614 is rotated so as to connect port 1612 to port 1670. Bottle 1660a is connected to port 1670 via tube 1674a, vacuum degassing unit 1676, and tube 1680a. A solvent conduit (not shown) similar to conduit 706 of FIG. 7 passes through vacuum gassing unit 1676 and connects tube 1674a to tube 1680a. The solvent conduit already contains a certain amount of degassed flush solvent from bottle 1660a. Syringe barrel 1650 is withdrawn to pull a suitable volume of the degassed flush solvent by syringe 1630. Multiport valve 1614 is rotated so as to connect port 1612 to port 1618. Syringe barrel 1650 is pushed in so as to expel the flush solvent into the waste container. This procedure of pulling in the flush solvent by syringe 1630 and expelling the flush solvent into the waste container is repeated until syringe 1630, tubes 1634 and 1644, and injector valve 1640 are considered flushed clean of any residual sample. Vacuum degassing unit 1676 in some embodiments is one of the vacuum degassing units described above with reference to FIGS. 4–15.

The flush solvent is degassed because gas in the flush solvent can adversely affect the performance of LC analytical system 710. Bubbles of gas can form in the flush solvent or the sample and cause inaccuracies in the amount of the sample drawn in by syringe 1630. When the sample amount is in the range of several microliters to several hundred microliters, the inaccuracies can be significant.

In some embodiments, syringe 1630 is replaced by some other means for pumping the flush solvent. In some embodiments, the same vacuum degassing unit 1676 is used to degas the mobile phase solvent and the flush solvent. That is, vacuum degassing unit 402 of FIG. 7 and vacuum degassing unit 1676 is one and the same vacuum degassing unit.

Figure 17:
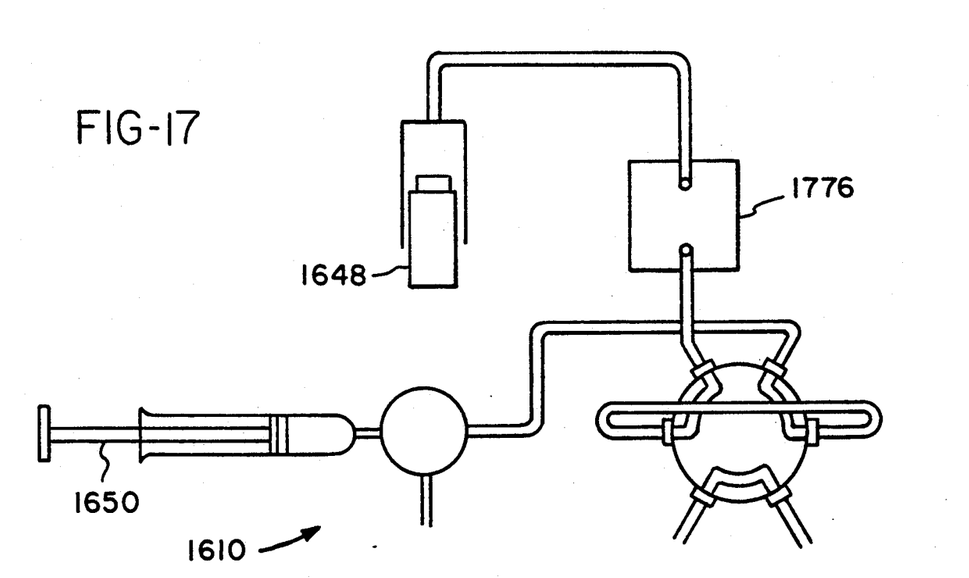
FIG. 17 shows a schematic diagram of another autosampler according to this invention.

FIG. 17 shows a portion of a variation of autosampler 1610 in which a vacuum degassing unit 1776 is used to degas the sample. The degassed sample is injected into the mobile phase or, alternatively, returned to the same or another sample container 1648 (by pushing syringe barrel 1650 in) for further processing. Vacuum degassing unit 1776 is used in some embodiments to degas flush solvents and the mobile phase.

Autosampler 1610 of FIGS. 16 and 17 is used also to dilute the sample in sample container 1648 by diluents and reagents. (A reagent is a solution that reacts with the sample.) Bottles 1660a, 1660b, and 1660c containing solvents or solutions that act as diluents and/or reagents are connected to respective ports 1670, 1690, and 1692 of multiport valve 1614 via respective tubes 1674a, 1674b and 1674c, via vacuum degassing unit 1676 and via respective tubes 1680a, 1680b and 1680c as shown in FIG. 16. Multiport valve 1614 is turned to connect port 1612 to port 1670, and syringe barrel 1650 is withdrawn by a predetermined distance to draw a predetermined amount of the solvent from bottle 1660a by syringe 1630. Multiport valve 1614 is then turned to connect port 1612 to port 1690, and syringe barrel 1650 is withdrawn further by a predetermined distance to draw a predetermined amount of the solvent from bottle 1660b by syringe 1630. Similarly, a predetermined amount of the solvent from bottle 1660c is drawn by syringe 1630. Multiport valve 1614 is then turned to connect port 1612 to port 1618, syringe barrel 1650 is pushed in, and the solvent mixture is delivered to sample container 1648. The sample diluted by the solvent mixture is then analyzed using liquid chromatography or other analytical methods.

In some applications, each solvent or solution is delivered to sample container 1648 separately. The solution from bottle 1660a is drawn by syringe 1630 and expelled into sample container 1648. Then the solution from bottle 1660b is drawn by syringe 1630 and expelled into sample container 1648. Then the solution from bottle 1660c is drawn in and expelled. In another variation, the solution from bottle 1660a is delivered to sample container 1648 separately, and the solutions from bottles 1660b and 1660c are drawn in one after another and then expelled together. Other variations are possible.

In some variations, more or less than three solutions are used. Multiport valve 1614 is replaced by a combination of valves in some embodiments.

In some embodiments, the same vacuum degassing unit 1676 is used to degas the diluents and the reagents, flush solvents, mobile phase solvents and the sample. In one variation, bottle 1660a contains a flush solvent, and bottles 1660b and 1660c contain diluent and reagent solvents. In some embodiments, several vacuum degassing units are used, each vacuum degassing unit for degassing one or more diluents, reagents, flush solvents and the mobile phase.

To summarize, autosampler 1610 is combined with one or more vacuum degassing units for sample preparation for chemical analysis and for sample injection where high precision in the sample preparation and injection is required. Additional tubing and plumbing is used as necessary to connect bottles and other containers with the sample and the solvents to the vacuum degassing units.

Figure 18:
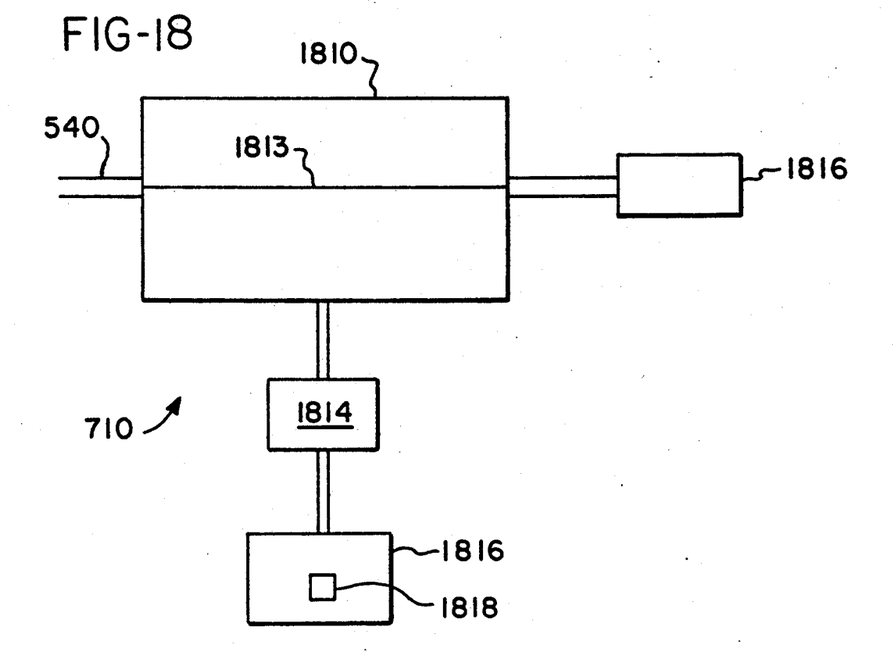
FIG. 18 shows a schematic diagram of a portion of a liquid chromatography analytical system according to this invention.

Gases dissolved in the sample being analyzed carry chromatographic information about the sample. Liquid chromatography analytical system 710 of FIG. 18 has its own vacuum chamber 1810 for extracting gas from the sample. The sample arrives via tubing 540, is degassed in vacuum chamber 1810 while in conduit 1813, and is conducted to column 1816 for further analysis. Vacuum pump 1814 creates vacuum in vacuum chamber 1810 and conducts the gas extracted from the sample to chamber 1816 where the gas is condensed. Gas sensor 1818 in chamber 1816 senses the gas and produces chromatographic information from the gas.

The walls of solvent conduit 706 of FIG. 7 become contaminated with time by particles suspended in the solvents. Such a contamination decreases the effectiveness of degassing. It is desirable to provide the user with a method for testing solvent conduit 706 so that the user could clean or replace the contaminated conduit. Conduit 706 is tested as follows. A gas is introduced into conduit 706 instead of a solvent. Vacuum pump 408 is operated until a predetermined level of vacuum is reached in vacuum chamber 406. Vacuum pump 408 is then turned off. The gas leaks out of conduit 706, and the vacuum level decays. The time of decay is measured, and the condition of conduit 706 is determined from the time of decay. The longer the time, the more contaminated conduit 706 is.

Sometimes it is desirable in liquid chromatography to use a mobile phase having certain gases dissolved in it. Vacuum degassing unit 402 of FIG. 7 is used to provide such a mobile phase. When the mobile phase (or a component thereof) is in solvent conduit 706, the gas is supplied under pressure into vacuum chamber 406 by vacuum pump 408. A portion of the gas permeates the walls of solvent conduit 706 and dissolves in the mobile phase. The mobile phase is then conducted to LC analytical system 710.

While the invention has been described with respect to the embodiments set forth above, other embodiments and variations not described herein are to be considered within the scope of the invention, as defined by the following claims.

What is claimed is:

1. A vacuum degassing unit for degassing a liquid, comprising:
   a vacuum chamber including a vacuum pump for creating a vacuum in said vacuum chamber;
   a source of liquid;

a bobbin in said chamber; and a first tube for conducting said liquid through said chamber, said first tube being wound in coils around said bobbin, the adjacent coils of said first tube being spaced from each other and said tube being permeable to gases in said liquid.

2. The vacuum degassing unit of claim 1, further comprising a second tube for conducting said liquid through said chamber, said second tube being permeable to gases in said liquid and wound in coils around said bobbin, the adjacent coils of said second tube being spaced from each other, and the coils of said first tube being spaced from the coils of said second tube on said bobbin.

3. A vacuum degassing unit for degassing a liquid, comprising:

a vacuum chamber including a vacuum pump for creating a vacuum in said vacuum chamber;

a source of liquid;

a plurality of tubes, each tube for conducting said liquid through said chamber; and a plurality of bobbins, each of said tubes having a portion wound around a corresponding one of said bobbins, said tubes being permeable to gases in said liquid.

4. An apparatus for providing degassed solvent to a liquid chromatography system comprising:

a liquid chromatography analytical system;

a source of solvent;

a vacuum degassing unit for degassing said solvent comprising a vacuum chamber including a vacuum pump for creating a vacuum in said vacuum chamber, a plurality of tubes, each tube for conducting said solvent through said chamber, and a plurality of bobbins, each of said tubes having a portion wound around a corresponding one of said bobbins, said tubes being permeable to gases in said solvent; and means for conducting the degassed solvent from said vacuum degassing unit to said analytical system.

* * * * *